United States Patent [19]

Ciganek et al.

[11] Patent Number: 4,579,952

[45] Date of Patent: Apr. 1, 1986

[54] INTERMEDIATES FOR OCTAHYDROBENZOFURO[3,2-E]ISOQUINOLINES

[75] Inventors: Engelbert Ciganek, Kennett Square, Pa.; Ashokkumar B. Shenvi, Wilmington, Del.

[73] Assignee: E. I. Du Pont de Nemours and Company, Wilmington, Del.

[21] Appl. No.: 517,238

[22] Filed: Jul. 25, 1983

Related U.S. Application Data

[62] Division of Ser. No. 334,838, Dec. 28, 1981, Pat. No. 4,415,736.

[51] Int. Cl.$^4$ .................. C07D 405/12; C07D 211/70
[52] U.S. Cl. .................................... 546/283; 546/339; 546/340
[58] Field of Search .................. 546/283, 339, 348

[56] References Cited

U.S. PATENT DOCUMENTS

| | | | |
|---|---|---|---|
| 2,748,140 | 5/1956 | Schmidle et al. | 546/348 |
| 2,886,570 | 5/1959 | Palopolli et al. | 546/348 |
| 3,125,488 | 3/1964 | Biel | 424/263 |
| 3,824,242 | 7/1974 | Levine et al. | 546/327 |
| 4,001,247 | 1/1977 | Zimmerman et al. | 546/144 |
| 4,001,248 | 1/1977 | Zimmerman et al. | 546/144 |
| 4,150,135 | 4/1979 | Ripka | 514/312 |
| 4,236,009 | 11/1980 | Zimmerman et al. | 546/112 |
| 4,243,668 | 1/1981 | Ciganek | 514/288 |
| 4,289,882 | 9/1981 | Rapoport et al. | 546/141 |

FOREIGN PATENT DOCUMENTS 2010806A 12/1978 United Kingdom ............ 546/112

OTHER PUBLICATIONS

Evans et al., *J. Am. Chem. Soc.* 102:5955 (1980).
Evans et al., *Tetrahedron Letters* 23:285 (1982).
Lewis et al., *J. Chem. Soc.* (C):1074 (1970).
Martin et al., *Tetrahedron Letters*, 3925 (1977).

*Primary Examiner*—Alan L. Rotman

[57] ABSTRACT

Process for preparing analgesic and narcotic antagonistic isoquinolines comprising:
(a) contacting and reacting a lithiated anisole or alkyl phenyl ether, optionally substituted at the 3-position to the lithium atom, with a 4-piperidone to yield a 4-aryl-4-piperidinol;
(b) dehydrating the piperidinol to a 4-aryl-1,2,3,6-tetrahydropyridine;
(c) metalating and acylating the 1,2,3,6-tetrahydropyridine to yield a 1-(4-aryl-1,2,3,4-tetrahydropyrid-4-yl)-4-hydroxy-1-butanone;
(d) reducing the ketone moiety of the butanone to yield a 5-aryl-7-oxa-2-azabicyclo[3.2.1]octane-6-propanol;
(e) converting the alcohol moiety of the propanol to L to yield a 5-aryl-6-[3-(L)propyl]-7-oxa-2-azabicyclo[3.2.1]octane in which L is a leaving group selected from the group consisting of —Cl, —Br, —I, p-MeC$_6$H$_4$SO$_3$— and MeSO$_3$—.
(f) opening the amino furan ring of the bicyclooctane to yield a 4-(L)-1-(4-aryl-1,2,3,4-tetrahydropyrid-4-yl)-1-butanol derivative;
(g) closing the 6-carbon ring of the butanol derivative by intramolecular reaction of the enamine and leaving group to yield a 4a-aryl-2,3,4,4a,5,6,7,8-octahydro-5-isoquinolinol or derivative thereof; and
(h) reducing the enamine double bond of the octahydro-5-isoquinolinol or derivative thereof to yield a 4a-aryldecahydro-5-isoquinolinol or derivative thereof and (i) cyclizing the decahydro-5-isoquinolinol or derivative to yield a 2,3,4,4a,5,6,7,7a-octahydro-1H-benzofuro[3,2-e]isoquinoline, or,
(h') cyclizing the octahydro-5-isoquinolinol or derivative thereof to yield a 2,3,5,6,7,7a-hexahydro-1H-benzofuro-[3,2-e]isoquinoline and (i') reducing the enamine double bond of the isoquinoline.

1 Claim, No Drawings

INTERMEDIATES FOR OCTAHYDROBENZOFURO[3,2-e]ISOQUINO-LINES

CROSS-REFERENCE TO RELATED APPLICATION

This application is a division of U.S. application Ser. No. 334,838 filed on Dec. 28, 1981, now U.S. Pat. No. 4,415,736 issued Nov. 15, 1983.

FIELD OF THE INVENTION

This invention relates to a process for preparing octahydrobenzofuro[3,2-e]isoquinoline analgesic and narcotic antagonistic compounds and intermediates of the process.

BACKGROUND OF THE INVENTION

Octahydrobenzofuro[3,2-e]isoquinoline analgesic and narcotic antagonistic compounds which can be prepared by the process of this invention are disclosed in U.S. Pat. No. 4,243,668. In that patent are disclosed the compounds having the following formula:

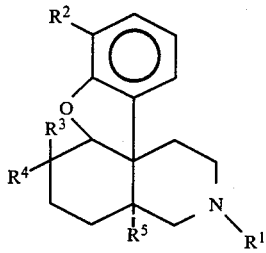

in which
$R^1$ is —H, $C_{1-10}$ alkyl, —$CH_2R^6$,

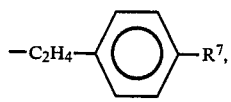

or —$(CH_2)_nCN$ in which n is 1-3;
$R^2$ is —H, —OH, $C_{1-12}$ alkoxy or $C_{2-12}$ acyloxy of an alkanoic acid;
$R^3$ is —H, —OH, —$CH_3$, $C_{1-2}$ alkoxy, $C_{2-12}$ acyloxy of an alkanoic acid, —F or —$N_3$;
$R^4$ is —H or —F;
$R^{3-4}$ in combination are methylene or keto;
$R^5$ is —H, —OH,

or —$OCH_3$;
$R^6$ is

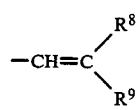

—C≡CH, $C_{3-6}$ cycloalkyl, 2-thienyl, 2-furyl or tetrahydrofuryl;
$R^7$ is $C_{1-3}$ alkyl, —$OCH_3$, —Cl, —Br or —F; and $R^8$ and $R^9$ are, independently, —H, —$CH_3$ or —Cl.
It is disclosed by way of example that $R^6$ may also be phenyl.

A process for preparing the compounds is disclosed in the patent, as are utility, dosage formulations and preferred compounds.

It is an object of this invention to provide a new process for preparing the isoquinoline compounds disclosed in said patent.

Zimmerman, et al., U.S. Pat. No. 4,236,009, disclose the following process: reaction of phenyllithium, optionally substituted at the meta-position, with a 1-alkyl- or 1-benzyl-4-piperidone; dehydration of the product to yield a 1-alkyl- or 1-benzyl-4-aryl-1,2,3,6-tetrahydropyridine; metalation to form a carbanion; addition of a propylene or butylene dihalide at the 4-position; and cyclization of the 4-substituted product with, e.g., sodium iodide in acetonitrile. Zimmerman, U.K. Patent Application No. 2,010,806, discloses similar reactions.

Evans, et al., *J. Am. Chem. Soc.* 102, 5955 (1980) disclose addition of allyl bromide or 1-bromo-4-chlorobutane at the 4-position of a 1-methyl-4-aryl-1,2,3,6-tetrahydropyridine carbanion followed by cyclization of the latter adduct with sodium iodide in acetonitrile. Levine, et al., U.S. Pat. No. 3,824,242, disclose a similar metalation followed by addition of ethyl haloformate. Lewis, et al., *J. Chem. Soc. (C)*, 1074 (1970) disclose lithium aluminum hydride reduction of the tetrahydropyridine substituted at the 4-position with ethoxycarbonyl to provide 2-methyl-5-phenyl-2-aza-7-oxabicyclo[3.2.1]octane.

DISCLOSURE OF THE INVENTION

For further comprehension of the invention, and of the objects and advantages thereof, reference may be had to the following description, and to the appended claims, in which the various novel features of the invention are more particularly set forth.

The invention resides in a process for preparing octahydrobenzofuro[3,2-e]isoquinoline analgesic and narcotic antagonistic compounds, Compound I, certain of which are disclosed and claimed in U.S. Pat. No. 4,243,668, which have the formula:

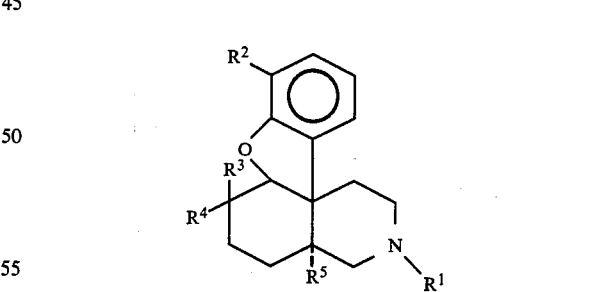

wherein
$R^1$ is $C_{1-10}$ alkyl, —$CH_2R^6$ or

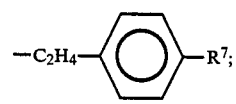

$R^2$ is —H, —OH or $C_{1-12}$ alkoxy;
$R^3$, $R^4$ and $R^5$ (not illustrated in the formulae below) are —H;

R[6] is $C_{3-6}$ cycloalkyl, phenyl or 2-tetrahydrofuryl optionally substituted with a methyl group; and R[7] is —H or $C_{1-3}$ alkyl.

More particularly, the invention resides in steps (a), (b) and (c), singly and in combination and in steps (a) through (i) in combination and intermediates III and IV of the process for preparing Compound I which is illustrated by the following reaction scheme, wherein, R[1] is as defined above;

R[2] is —H or $C_{1-12}$ alkoxy or, in Compound XI, R[2] may be —OH;

R[10] is $C_{1-10}$ alkyl;

R[11] is —OH, $C_{1-3}$ alkyl carbonyloxy, —Cl, —Br, —I, p-MeC$_6$H$_4$SO$_3$— or MeSO$_3$;

R[12] and R[13] are —H or $C_{1-3}$ alkyl and taken together may form a $C_{2-5}$ alkylene group, optionally substituted with a methyl group, except that R[12] and R[13] may not both be —H;

R[14] is —OH, Me$_3$SiO— or t-BuMe$_2$SiO—;

R[15] is $C_{1-3}$ alkyl carbonyloxy or —OCH(R[12])OR[13], or, in Compounds IX and X, R[15] may be R[11], or, R[11] or R[14], respectively;

L is —Cl, —Br, —I, p-MeC$_6$H$_4$SO$_3$— or MeSO$_3$—; and a is — or ⹀,

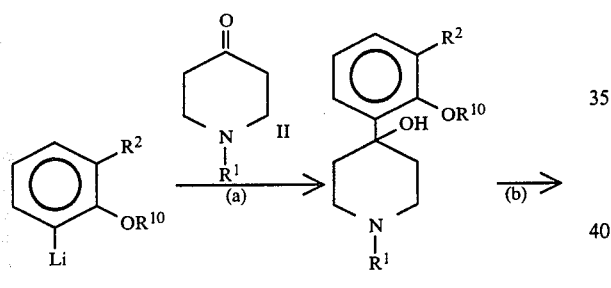

III

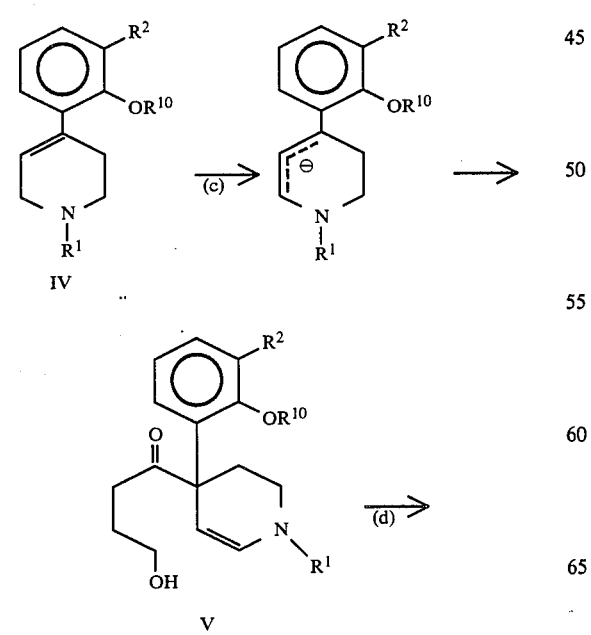

IV

V

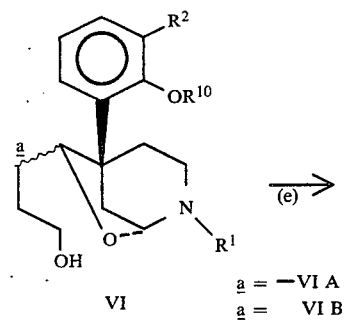

VI a = —VI A
a = ⹀ VI B

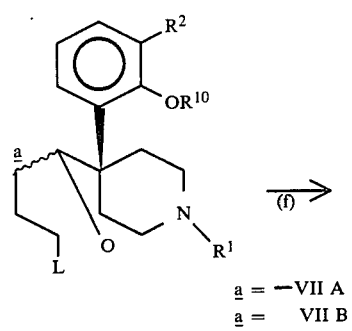

a = —VII A
a = ⹀ VII B

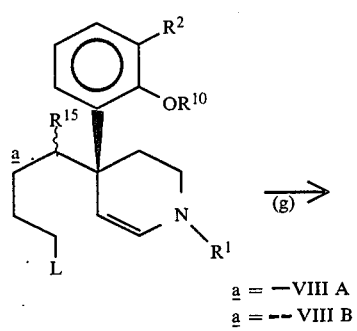

a = —VIII A
a = ⹀ VIII B

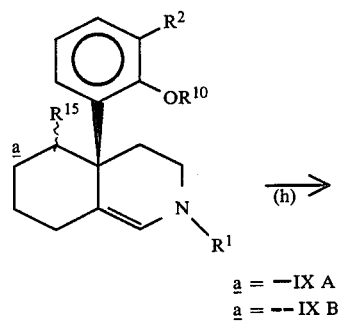

a = —IX A
a = ⹀ IX B

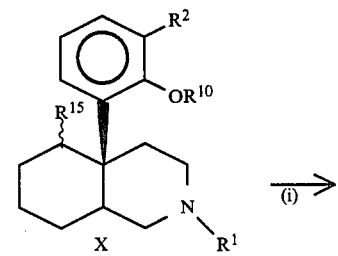

X

-continued

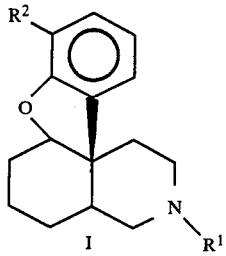

In a modified illustrative scheme, steps (h) and (i) are replaced by (h') and (i') as follows:

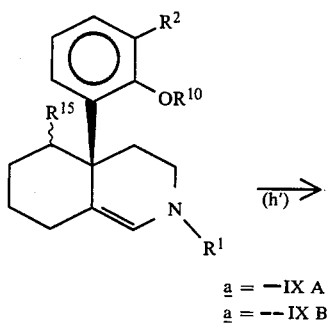

$\underline{a}$ = —IX A
$\underline{a}$ = ---IX B

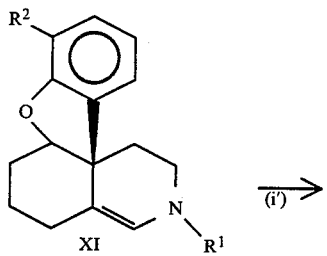

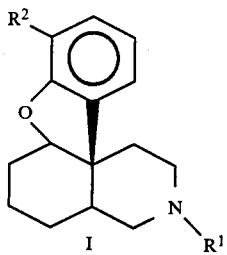

It will be noted that Compound I in which $R^7$ is —H is not disclosed in U.S. Pat. No. 4,243,668. This compound is similar, in utility and manner of use, to the compounds which are disclosed in said patent.

Following is a further description of the above-illustrated scheme and identification of the compounds and processes comprising the invention.

The invention resides in the above-illustrated Compound III and Compound IV. The invention also resides in the above-illustrated process steps (a), (b) and (c) singly and in combination and steps (a) through (i) in combination.

Steps (h) and (i) comprise cyclizing and reducing the enamine double bond of a 4a-aryl-2,3,4,4a,5,6,7,8-octahydro-5-isoquinolinol or derivative thereof, e.g., acetate, illustrated as Compound IX. This process may be carried out in any sequence, i.e., it may comprise (h) reducing the enamine double bond of the octahydro-5-isoquinolinol or derivative to yield a 4a-aryldecahydro-5-isoquinolinol or derivative thereof, e.g., Compound X, and (i) cyclizing the latter compound to yield the desired isoquinoline; or, it may comprise (h') cyclizing the octahydro-5-isoquinolinol or derivative to yield a 2,3,5,6,7,7a-hexahydro-1H-benzofuro[3,2-e]isoquinoline, e.g., Compound XI, and (i') reducing the enamine double bond of the latter compound to yield the desired isoquinoline.

With reference to the illustrative scheme, Compound IX is reduced to Compound X in step (h) in the presence of a hydrogenation catalyst such as $PtO_2$, which may be supported, in an alcohol or inert solvent. This step is illustrated in Example 17.

In step (i), a furan ring is formed under basic conditions, as illustrated in Examples 18 and 23, or acidic conditions as illustrated in Example 19 to form Compound I.

Under acidic conditions, the functional group, $R^{15}$, can be used directly or after conversion to $R^{14}$, i.e., hydroxy or silyl ether. Under basic conditions, the functional group, $R^{15}$, if it is not $C_{1-3}$ alkyl carbonyloxy, is first converted to $R^{11}$. The hydroxy functional group can be prepared by hydrolysis of $R^{15}$. The silyl ethers can be prepared by treating the hydroxy derivative with a silyl chloride in the presence of base in an inert solvent. The sulfonate ester derivatives can be prepared directly from the hydroxy derivatives as in step (e). The halogen derivative can be prepared by treating the hydroxy derivative with a halogenating agent as in step (e), or by displacing the sulfonate group of the sulfonate ester derivative.

Conversion to Compound I under acidic conditions is accomplished by treating with a protic or Lewis acid in an inert or polar solvent at 0° to 100° C. This reaction will yield Compound I in which $R^2$ is —H or $C_{1-12}$ alkoxy. When $R^2$ is $C_{1-12}$ alkoxy, it can be converted to —H or —OH by standard techniques.

Under basic conditions, the conversion is accomplished by treatment with a lower alkyl mercaptide salt of an alkali metal in a polar solvent at 50° to 200° C. This reaction will yield Compound I in which $R^2$ is —H or —OH. When $R^2$ is —OH it can be converted to —H or $C_{1-12}$ alkoxy by known techniques.

Preferably, the furan ring is formed under basic conditions because better yields result. Under acidic conditions, e.g., Example 19, the yield of Compound I is about 10% whereas under basic conditions, e.g., Example 23, the yield is about 90%.

In step (h), the reduction of Compound IX B in which a is ---does not result in significant amounts of Compound X. Compounds IX A and/or IX B can be converted to a compound having a furan ring, the isoquinoline Compound XI, in which $R^2$ is —H or —OH, under the preferred, i.e., basic, conditions, in a reaction similar to the reaction described above in step (i) in which Compound X is converted to Compound I under basic conditions. This reaction results in higher yields of Compound XI from Compound IX A than from Compound IX B.

Compound XI can be reduced to Compound I in a reaction similar to the reaction described above in step (h) in which Compound IX is reduced to Compound X. In this reaction, slight contamination of Compound XI with sulfur compounds from the mercaptide salt may retard the rate of reduction of the enamine double bond. To avoid this problem, the product mixture containing Compound XI may be treated with Raney ® nickel to remove any sulfur-containing impurities.

The isoquinolinol or derivative thereof used in steps (h) and (h'), illustrated as Compound IX, is prepared in step (g) by closing the 6-carbon ring of a 4-(L)-1-(4-aryl-1,2,3,4-tetrahydropyrid-4-yl)-1-butanol derivative, e.g., acetate, by intramolecular reaction of the enamine and L. L is a leaving group and is defined above.

With reference to the illustrative scheme, the reaction is effected by refluxing a solution of Compound VIII A in which a is — and/or Compound VIII B in which a is $\cdots$, in the presence of an organic or inorganic base, such as potassium carbonate, in an inert solvent, such as acetonitrile.

If the starting material is Compound VIII B, a reaction time of 1 hour is critical to obtaining the optimum yield of Compound IX B. Shorter reaction times result in low conversion of starting material and longer reaction times result in low yield of Compound IX B.

Similar reactions are disclosed in U.K. Specification No. 2,010,806, U.S. Pat. No. 4,236,009 and Evans, et al., *J. Am. Chem. Soc.* 102, 5655 (1980).

The above-cited references suggest the use of an iodide salt such as sodium or lithium iodide to accelerate a similar reaction. This step is illustrated in Examples 15 and 16.

The butanol derivative used in step (g), illustrated as Compound VIII, is prepared in step (f) by opening the amino furan ring of a 5-aryl-6-[3-(L)-propyl]-7-oxa-2-azabicyclo[3.2.1]octane.

With reference to the scheme, in this step, the amino furan ring of Compounds VII A or VII B, or the hydrohalide salt thereof, is opened by treating the compound with a reagent that reacts at the oxygen of the furan ring to provide an oxygen functionality, and simultaneously liberates the enamine functionality, e.g., an anhydride of a lower alkyl carboxylic acid or an enol ether compound in the presence of a protic or Lewis acid at 0° to 100° C.

The preferred starting material is the hydrohalide salt of Compound VII A since this compound can be used without liberating the free base. The hydrobromide is especially preferred for reasons of convenience. If Compound VII A is used, the reaction is preferably carried out at 70° to 80° C.; if Compound VII B is used, the reaction is preferably carried out at ambient temperature.

An example of an anhydride and an acid which can be used in the reaction is acetic anhydride and trifluoroacetic acid; examples of an enol ether are 2-methoxypropene and dihydropyran.

This step is illustrated in Examples 13 and 14.

The octane used in step (f), illustrated as Compound VII, is prepared in step (e) by converting the alcohol moiety of a 5-aryl-7-oxa-2-azabicyclo[3.2.1]octane-6-propanol to L. It is preferred that this step be carried out using Compound VI A because it is crystalline.

In this step, L is introduced to the compound at the position occupied by the alcohol functionality. This step is illustrated in Examples 10 to 12, below.

If a halogen leaving group is desired, a halogenating reagent such as a triphenylphosphinedihalogen complex in which the halogen is chlorine or bromine can be used. Such a halogenating agent can be prepared by treating triphenylphosphine with the halogen in an inert solvent.

If a sulfonate leaving group is desired, the propanol, e.g., Compound VI, can be treated with a sulfonyl chloride such as p-toluenesulfonyl chloride or methanesulfonyl chloride in the presence of an organic base such as pyridine or triethylamine or an inorganic base in an inert solvent at $-30°$ to 0° C. Alternatively, the propanol can be treated with a lower alkyl sulfonate ester at 50° to 200° C. The sulfonate esters may be used in step (f) or may be converted to halides, such as by treatment with an alkali metal halide in an inert solvent, which can be used in step (f).

The propanol used in step (e), illustrated as Compound VI, is prepared in step (d) by reducing the ketone moiety of a 1-(4-aryl-1,2,3,4-tetrahydropyrid-4-yl)-4hydroxy-1-butanone, illustrated as Compound V.

A similar reaction is disclosed in Lewis, et al., *J. Chem. Soc.* (C), 1074 (1970). This step is illustrated in Examples 6 to 9.

The reduction can be effected by treatment with a complexed aluminum hydride in an inert solvent or an alkali or alkaline earth metal in an alcohol solvent at $-72°$ C. to the reflux temperature. The product, Compound VI, exists as two diastereomers, VI A, in which a is — and VI B, in which a is $\cdots$. The relative amounts of the diastereomers depend upon the reducing reagent and upon the temperature.

Compound VI A can be isolated in high purity from the product mixture by crystallizing its hydrochloride salt which is produced by treating a solution of the product mixture, preferably in ether or methanol, with hydrogen chloride. The resulting mother liquor contains Compounds VI B and VI A. The hydrochloride salt of Compound VI A may be used in step (e) or may be treated with base, such as a sodium carbonate solution, to form the free base, Compound VI A.

The preferred method for the preparation of Compound VI B is to effect the reduction at $-72°$ C. with lithium aluminum hydride.

The butanone used in step (d) is prepared in steps (a), (b) and (c) which comprise:

(a) contacting and reacting a lithiated anisole or alkyl phenyl ether, optionally substituted at the 3-position to the lithium atom, with a 4-piperidone to yield a 4-aryl-4-piperidinol;

(b) dehydrating the piperidinol to a 4-aryl-1,2,3,6-tetrahydropyridine; and, (c) metalating and acylating the 1,2,3,6-tetrahydropyridine.

Following is a further description of these three steps:

Step (a): Step (a) is a Grignard reaction similar to reactions disclosed in U.K. Specification No. 2,010,806, U.S. Pat. No. 4,236,009 and Evans, et al., *J. Am. Chem. Soc.* 102, 5655 (1980). This step is illustrated in Examples 1 and 2, below.

The reaction is typically carried out at 0° to 25° C., although temperatures as low as about $-72°$ C. may be used, in an inert solvent, such as tetrahydrofuran, for about 1 to 12 hours, usually about 3 hours. The resulting Compound III can be isolated by known techniques such as crystallization as in Example 1 or removal of unreacted starting materials under vacuum as in Example 2.

Lithiated anisoles or alkyl phenyl ethers, can be prepared by treating the corresponding aryl ethers with a $C_{1-8}$ alkyl lithium compound in an inert solvent at $-72°$ to 25° C., or, by metal halogen exchange of a compound which is substituted with halogen at a position adjacent the ether functionality by treatment with a $C_{1-8}$ alkyl lithium compound in an inert solvent.

Step (b): Step (b) is a dehydration reaction. Similar reactions are disclosed in U.K. Specification No.

2,010,806, U.S. Pat. No. 4,236,009 and Evans, et al., *J. Am. Chem. Soc.* 102, 5655 (1980). This step is illustrated in Examples 3 and 4, below.

This reaction is preferably carried out in a strong acid at about 45° to 65° C. for about 3 hours. The use of higher temperatures results in undesirable side products. The above-cited references suggest that a dehydrating agent, e.g., phosphorus pentoxide and methanesulfuric acid, may be employed.

Step (c): Step (c) involves metalation followed by acylation. Similar metalations of allylamines are disclosed in U.S. Pat. Nos. 3,824,242 and 4,236,009, U.K. Specification No. 2,010,806, Martin, et al., *Tetrahedron Letters*, 3925 (1977) and Evans, et al., *J. Am. Chem. Soc.* 102, 5655 (1980). A similar acylation of a metalated allylamine is disclosed in U.S. Pat. No. 3,824,242. This step is illustrated in Example 5, below.

The metalation may be effected by treatment with a $C_{1-8}$ alkyl lithium compound such as n-butyl lithium in an inert solvent at $-72°$ to $0°$ C., preferably $-10°$ C., to form the carbanion.

The acylation may be effected by adding the anion to a solution of γ-butyrolactone in an inert solvent at $-72°$ to $0°$ C. The resulting keto alcohol may be isolated by treatment with a basic hydroxide in an alcohol solvent as in Example 5 or it may be used in step (d) without isolation as in Example 6.

The invention resides in steps (a), (b) and (c) singly and in combination and in the process comprising combined steps (a) through (i). The invention does not reside in steps (d) through (i), as these steps were invented by an inventive entity other than the inventive entity herein.

Other useful derivatives of Compound I can be prepared by converting the substituents by known techniques, some of which are disclosed in U.S. Pat. No. 4,243,668. These include the derivatives in which:

$R^1$ is $-(CH_2)_nCN$;
$R^2$ is $C_{2-12}$ acyloxy;
$R^5$ is $-OH$,

or $-OCH_3$;
$R^6$ is

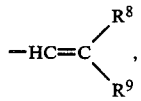

$-C≡CH$, 2-thienyl or 2-furyl, optionally substituted;
$R^7$ is $-OCH_3$ or $-Cl$, $-Br$ or $-F$; and
$R^8$ and $R^9$ are, independently, $-H$, $-CH_3$ or $-Cl$.

The derivative in which $R^5$ is $-OH$ may be prepared by hydroborating the enamine double bond with borane or its derivatives by basic peroxide oxidation of the resulting borane. The acetoxy and methoxy derivatives are prepared therefrom by known techniques.

EXAMPLES

The following examples are illustrative of steps of the above-described process. The steps being illustrated are indicated after the title of each example. Examples 1 through 5 illustrate steps (a) through (c) which are useful in preparing compounds useful in step (d). Examples 6 through 23 illustrate steps (d) through (i).

Temperature is in °C. and, except where noted, percentages are by weight. Except where otherwise noted, $R^1$ and $R^{10}$ are $-CH_3$ and $R^2$ is $-OCH_3$. The Compounds III to XI used in the examples were prepared substantially by the procedures illustrated in other examples.

EXAMPLES 1 AND 2

Synthesis of 4-(2,3-Dimethoxyphenyl)-1-methyl-4-piperidinol (Step a)

1. A solution of 138 g (1.0 mol) of veratrole in 400 mL of dry tetrahydrofuran was cooled to 0° and treated with 500 mL of 1.65M (0.82 mol) n-butyl lithium over a period of 30 min at such a rate that the temperature of the reaction mixture remained below 20°. After the addition was complete the reaction mixture was stirred at room temperature for 16 hours. At the end of this period the reaction mixture was cooled to $-5°$ and 90.4 g (0.8 mol) of 1-methyl-4-piperidone was added over a period of 60 min at a rate such that the temperature of the reaction mixture was kept below 5°. After the addition was complete the reaction mixture was stirred at room temperature for 3 hours. At the end of this period the reaction mixture was quenched with 400 mL of water and divided into two portions. Each portion was diluted with 200 mL of ether. The organic layers were each washed with 100 mL of brine and the combined aqueous layers were extracted with portions of dichloromethane (3×175 mL). The combined organic layers were dried ($K_2CO_3$) and concentrated under reduced pressure to afford 206.0 g of an oil which upon trituration with 400 mL of hexane afforded 73.5 g of a white solid, mp 66°–76° (36% yield) which may be used without further purification for the next conversion. A sample prepared in a similar experiment was purified by crystallization to obtain Compound III as a solid, mp 81–81.5° C.; NMR (90 MHz, CDCl$_3$): 2.33 (s, 3), 3.86 (s, 3), 3.96 (s, 3), 4.2–4.4 (br., 1). IR (KBr): 2970, 1580 cm$^{-1}$.

2. A solution of 138 g (1.0 mol) of veratrole in 400 mL of dry tetrahydrofuran was cooled in a dry ice/acetone bath and treated with 500 mL of 1.6M solution (0.82 mol) of n-butyl lithium at such a rate that the temperature of the reaction mixture remained at 0°. After the addition was complete the reaction mixture was stirred at room temperature for 3 hours. At the end of this period the resulting white slurry was cooled in a dry ice/acetone bath and 90.4 g (0.8 mol) of 1-methyl-4-piperidone was added at such a rate that the temperature of the reaction mixture remained below $-10°$. After the addition was complete the reaction mixture was stirred at 0° for 2 hours, quenched with 400 mL of water and diluted with 400 mL of ether. The organic layer was separated and the aqueous layer was extracted with dichloromethane (3×400 mL). The combined organic layers were dried ($K_2CO_3$) and concentrated under reduced pressure to afford 270.9 g of an oil. This oil was distilled under reduced pressure to remove all the material boiling below 150°/0.025 mm (3.3 Pa). The remaining residue, 97.55 g, contained the desired Compound III and was used without further purification in the next step.

EXAMPLES 3 AND 4

Synthesis of 4-(2,3-Dimethoxyphenyl)-1,2,3,6-tetrahydro-1-methyl-pyridine (IV) (Step b)

3. A solution of 79.49 g (0.316 mol) of Compound III, in 238 mL of concentrated hydrochloric acid was heated to 65° for 3 hours. At the end of this period, the reaction mixture was cooled to room temperature and made basic with 20% sodium hydroxide solution and extracted with dichloromethane (3×200 mL). The organic layers were dried ($K_2CO_3$), combined and concentrated under reduced pressure. The product thus obtained was distilled under reduced pressure to afford Compound IV as a colorless oil bp 100°–122°/0.05 mm (6 Pa) 73.56 g (84.8% yield). Samples prepared in other experiments performed in substantially the same manner showed IR (film): 2940, 1570 cm$^{-1}$; NMR (90 MHz, CDCl$_3$): 2.4 (s, 3), 3.76 (s, 3), 3.83 (s, 3), 5.8 (t,J=3 Hz, 1), 7.7–7.1 (br., 3).

4. A solution of 97.55 g of Compound III from Example 2, in 292 mL of concentrated hydrochloric acid was heated at 65° for 3 hours. At the end of this period, the reaction mixture was cooled to room temperature and made basic with 20% sodium hydroxide solution (800 mL). Extraction with dichloromethane (3×400 mL), drying ($K_2CO_3$) and concentration under reduced pressure afforded an oil. This oil was distilled under reduced pressure to afford 67.30 g Compound IV, bp 120°–125°/0.1 mm (10 Pa) (36% yield based on Compound II).

4A. A solution of 0.2 g of Compound III in 2 mL of trifluoroacetic acid was heated under reflux for 1 hour. Excess acid was removed under vacuum. A residue was dissolved in methylene chloride and the solution was washed with aqueous sodium hydroxide solution and dried. Removal of the solvent yielded 0.2 g of essentially pure Compound IV.

Dehydration of Compound III in trifluoroacetic acid was found to proceed at room temperature with a half-reaction time of about 70 min.

EXAMPLE 5

Synthesis of 1-[4-(2,3-Dimethoxyphenyl)-1,2,3,4-tetrahydro-1-methylpyrid-4-yl]-4-hydroxy-1-butanone (V) (Step c)

A solution of 9.32 g (0.04 mol) of the allylamine, Compound IV, in 75 mL of dry tetrahydrofuran was cooled to −10° and treated with 40 mL of 1.65M solution (0.066 mol) of n-butyl lithium. The resulting red solution was stirred at −10° for 15 min and transferred under nitrogen to a solution of 18.4 g (0.21 mol) of γ-butyrolacetone in 40 mL of dry tetrahydrofuran at −76° over a period of 5 min. After the addition was complete the reaction mixture was stirred at −70° for 15 min and then quenched with 100 mL of 20% sodium hydroxide solution and stirred at room temperature for 1 hour. At the end of this period the reaction mixture was diluted with 200 mL of dichloromethane and the organic layer was separated. The aqueous layer was extracted with an additional 200 mL portion of dichloromethane. The organic layers were washed with brine, dried ($K_2CO_3$) and concentrated under reduced pressure to afford 12.6 g of product (98.8% yield) which contained Compound V and was used for the next step without further purification. A sample prepared in another experiment was purified by HPLC to afford a pure sample of Compound V; NMR (90 MHz, CDCl$_3$): 2.63 (s, 3), 3.45 (br., 3), 3.73 (s, 3), 3.88 (s, 3), 4.3 (d, j=8 Hz, 1), 6.15 (d, J=8 Hz, 1), 6.7–7.2 (br., 3); IR (film): 3440, 2940, 1700, 1630 cm$^{-1}$.

EXAMPLE 6

Synthesis of (1R*,5R*,6R*)-5-(2,3-Dimethoxyphenyl)-2-methyl-7-oxa-2-azabicyclo[3.2.1]-octane-6-propanol (VIB) (Steps c and d)

A solution of 67.30 g (0.29 mol) of Compound IV in 450 mL of dry tetrahydrofuran was cooled to −10° and treated with a slow stream of 198 mL of 1.6M solution (0.32 mol) of n-butyl lithium over about 20 min so that the temperature of the reaction mixture remained below 5°. After the addition was complete the resulting red solution was stirred at −10° for 15 min and then added under nitrogen to a solution of 40.86 g (0.475 mol) of γ-butyrolactone in 100 mL of dry tetrahydrofuran which had been cooled to −72°. The resulting pale brown solution was stirred at −72° for 1 hour and then transferred to a suspension of 18.05 g (0.475 mol) of lithium aluminum hydride in 150 mL of dry tetrahydrofuran at −72°. After the addition was complete, about 20 min, the reaction mixture was stirred at −10° for 1 hour, warmed to room temperature and quenched with 18 mL of water followed by 54 mL of 20% sodium hydroxide. The resulting slurry was filtered and the residue was washed with dichloromethane (4×200 mL). The filtrates were dried ($K_2CO_3$) and concentrated under reduced pressure to obtain 109.9 g of product. The product was heated to 80° at 0.2 mm (30 Pa) pressure to remove any volatile impurities; 103.6 g of product containing Compound VI B was obtained. It was used in the next step without further purification. The ratio of the two diastereomers VI A and VI B in the product of another similar experiment was estimated by NMR to be approximately 1:3. A sample prepared in another similar experiment was purified by chromatography to afford a pure sample of Compound VI B; NMR (90 MHz, CDCl$_3$): 2.33 (s, 3), 3.83 (s, 6), 4.1–4.4 (br., 1), 4.70 (d, J=6 Hz, 1), 6.6–7.1 (br., 3).

EXAMPLES 7, 8 AND 9

Synthesis of (1R*,5S*,6R*) and (1R*,5R*,6R*)-5-(2,3-Dimethoxyphenyl)-2-methyl-7-oxa-2-azabicyclo[3,2,1]octane-6-propanol, (VIA and VIB) (Step d)

7. To a suspension of 5.0 g (0.13 mol) of lithium aluminum hydride in 100 mL of dry tetrahydrofuran at −10° was added a solution of 32.93 g of the keto alcohol, Compound V, in 50 mL of dry tetrahydrofuran. After the addition was complete, the reaction mixture was stirred at −10° for 1 hour and then worked up by adding 8 mL of water followed by 24 mL of 20% sodium hydroxide solution. The slurry thus produced was filtered and the residue was washed with dichloromethane (5×50 mL). The combined filtrates were dried ($K_2CO_3$) and concentrated under reduced pressure to afford 30.82 g of an oil. This material was purified by using flash column chromatography over silica gel. Elution with 1:1 hexane-acetone (v/v) mixture containing 5% triethylamine afforded 19.95 g (62% yield) of a mixture of Compounds VI A and VI B. The separation of the two diastereomers was achieved as follows. The material was dissolved in 200 mL of ether and the solution was treated with 25 mL of methanol saturated with hydrogen chloride. Solvent was evaporated from the resulting solution and the residual oil was dissolved in a minimum amount of methanol. About 200 mL of ether was added to this solution until a slight turbidity appeared and then the solution was warmed until clear. Upon cooling for about 18 hours, 3.4 g of a white solid separated out. The mother liquor was allowed to stand in a container also containing ether for 46 hours and the precipitated solid was collected. The combined solid, 8.15 g (22% yield) contained mostly Compound VI A hydrochloride salt, mp 205°–208°. The mother liquor from the crystallization was concentrated under reduced pressure, dissolved in dichloromethane and shaken with 100 mL of saturated $Na_2CO_3$. The aqueous layer was extracted with dichloromethane (2×100 mL). The combined organic layers were dried ($K_2CO_3$) and concentrated under reduced pressure to obtain 12.35 g of an oil containing mostly Compound VI B.

8. To a suspension of 20 g (0.51 mol) of lithium aluminum hydride in 200 mL of dry tetrahydrofuran at −10° to 0° was added 124.55 g (0.39 mol) of Compound V in 250 mL of dry tetrahydrofuran. After the addition was complete the reaction mixture was stirred at 0° for 1 hour and then sequentially quenched with 20 mL of water, 60 mL of 20% sodium hydroxide solution and 20 mL of water. The resulting slurry was filtered and the residue was washed with dichloromethane. The combined filtrates were concentrated under reduced pressure to afford 125 g of product. This material was dissolved in 200 mL of ether and treated with 100 mL of ethanol saturated with hydrogen chloride. Part of the solvent from the resulting mixture was removed under reduced pressure and the slurry thus generated was diluted with 25 mL of methanol. Upon filtration 55 g of a solid was obtained which was recrystallized from 200 mL of methanol to afford 26.7 g of a solid, mp 209°–212°. The mother liquor from the recrystallization afforded an additional 3.0 g of a solid. The total yield of the solid was 29.7 g (8.2%). The solid, mp 205°–208°, prepared in a similar experiment, was found to contain Compounds VI A:VI B in a ratio of 91:9. The solid, Compound VI hydrochloride, prepared in another similar experiment showed NMR (90 MHz, $CDCl_3$): 3.80 (s, 3), 3.90 (s, 3), 4.66 (d,d, J=9, 3 Hz, 1), 5.05 (d, J=6 Hz, 1), 6.6 (d,d, J=6, 3 Hz, 1), 6.8–7.1 (br., 3).

8A (Free base). A sample of a Compound VI A hydrochloride in dichloromethane was treated with saturated sodium carbonate, dried and evaporated to obtain the free base, Compound VI A; NMR (90 MHz, $CDCl_3$): 2.36 (3, s), 3.5 (t, J=6 Hz, 2), 3.86 (s, 3), 3.90 (s, 3), 4.40 (d,d, J=9, 3 Hz, 1), 4.70 (d, J=6 Hz, 1), 6.57–7.03 (br., 3), IR: (film) 3400, 2940, 1580 cm$^{-1}$.

8B (Formate esters). Approximately 0.10 g (0.3 mmol) of crystals of Compound VI A, separated from a mixture of Compounds VI A and VI B was dissolved in 5 mL of formic acid and about 3 drops of trifluoroacetic acid were added. The reaction mixture was stirred at room temperature for 2 hours. At the end of this period the reaction mixture was made basic with saturated sodium carbonate solution and extracted with 100 mL of dichloromethane. The organic layer was dried ($K_2CO_3$) and concentrated under reduced pressure to afford the formate ester whose NMR was used for the estimation of the relative ratios of VI A and VI B. The NMR spectrum showed the presence of two peaks, one at 9.97 ppm and the other at 8.03 ppm corresponding to an 88:12 ratio of Compounds VI A:VI B, respectively. A sample purified by column chromatography showed NMR (90 MHz, $CDCl_3$): 2.33 (two peaks, 3), 3.8 (two peaks, 6), 3.9–4.5 (br., 3), 4.7 (t, J=6 Hz, 1), 6.6–7.1 (br., 3); IR (film): 2940, 1720, 1580, cm$^{-1}$.

9. A solution of 0.319 g (1.00 mmol) of Compound V in 25 mL of isopropanol was treated with approximately 1.0 g (43 mg atom) of sodium and refluxed for 1.5 hour. At the end of this period, the reaction mixture was quenched with water, extracted with 2×100 mL of dichloromethane, dried ($K_2CO_3$) and concentrated under reduced pressure to afford 0.290 g (90% yield) of product. The ratio of the two diastereomers VI A and VI B in the product was 43.57.

EXAMPLES 10, 11 AND 12

Synthesis of (1R*,5S*,6R*) and (1R*,5R*,6R*)-6-(3-bromopropyl)-5-(2,3-Dimethoxyphenyl)-2-methyl-7-oxa-2-azabicyclo[3,2,1]octane (VII A and VII B; L=Br) (Step e)

10 (VII A). A suspension of 11.60 g (0.032 mol) of Compound VI A hydrochloride salt in 100 mL of dry tetrahydrofuran was treated with 10.20 g (0.039 mol) of triphenylphosphine and cooled in water. To this suspension, 6.22 g (0.039 mol) of bromine was added. After stirring the reaction mixture for 15 min, 10 mL of methanol was added and the reaction mixture was concentrated under reduced pressure to obtain a solid product. This product was suspended in 200 mL of toluene and filtered to obtain 9.15 g of a solid. The toluene from the mother liquor was removed under reduced pressure and the resulting residue was treated with 25 mL of toluene. The resulting slurry was filtered and the residue was washed with 25 mL of toluene. The solid thus obtained was again suspended in 25 mL of toluene and filtered to afford 2.61 g of the hydrobromide salt of Compound VII A. The total yield of the desired Compound VII A hydrobromide was 11.76 g (78% yield). This hydrobromide salt was used for the next reaction without further purification or liberation of the free amine. A sample was crystallized from methanol in ether to obtain crystals, mp 162°–164°, NMR (90 MHz, $CDCl_3$): 2.77 (s, 3), 3.83 (s, 3), 3.90 (s, 3), 4.66 (d,d, J=9, 3Hz, 1), 5.16 (d, J=6 Hz, 1), 6.66 (d,d, J=6, 3Hz, 1), 6.8–7.1 (br., 2); Anal. Calcd. for $C_{18}H_{27}NO_3Br_2$: C, 46.4; H, 5.8; N, 3.0; Br, 34.4; Found: C, 46.67; H, 5.88; N, 2.85; Br, 30.31.

11 (VII A). A solution of 1.88 g (5.85 mmol) of Compound VI A in 20 mL of dry tetrahydrofuran was added to a solution of 1.84 g (7.0 mmol) of triphenylphosphine in 10 mL of dry tetrahydrofuran. To this reaction mixture was added 1.12 g (7.0 mol) of bromine and the mixture stirred at room temperature for 15 min. At the end of this period the reaction mixture was diluted with 30 mL of toluene and washed with 10% hydrochloric acid (3×25 mL). The aqueous layer was made basic with sodium carbonate and then extracted with dichloromethane (5×50 mL). The dichloromethane layer was dried and concentrated under reduced pressure to obtain 2.73 g of an oil which contained Compound VII A and was used without further purification for the next step.

12 (VII B). A solution of 4.9 g (15.2 mmol) of free Compound VI B in 40 mL of dry tetrahydrofuran and containing 4.78 g (18.2 mmol) of triphenylphosphine was treated with 2.9 g (18.2 mmol) of bromine. The reaction mixture was stirred for 15 min, diluted with 40 mL of toluene and extracted with 10% hydrochloric acid (3×75 mL). The aqueous layers were made basic with saturated solution of sodium carbonate and extracted with dichloromethane (5×50 mL). The organic layers were dried, combined and concentrated under reduced pressure to afford 7.00 g of an oil which contained Compound VII B and was used in the next step without further purification.

EXAMPLES 13 AND 14

Synthesis of [1S*,(4R*)] and [1R*,(4R*)]-4-bromo-1-(4-[2,3-dimethoxy-phenyl]1,2,3,4-tetrahydro-1-methylpyrid-4-yl)-1-butanol, acetate (VIII A and VIII B; $R^{15}$=Acetate)

(Step f)

13 (VIII A). A solution of 11.76 g (0.025 mol) of the hydrobromide VII A, from Example 10, in 50 mL of a 1:1 mixture of acetic anhydride and trifluoroacetic acid (v/v) was heated at 80° for 16 hours. At the end of this period the reaction mixture was cooled to room temperature and the solvent was removed under vacuum. The resulting oil was stirred with 100 mL of water for 15 min, made basic with a saturated solution of sodium carbonate and extracted with dichloromethane (3×100 mL). The combined organic layers were dried ($K_2CO_3$) and evaporated to afford 7.4 g (69% yield) of a semisolid product. A sample prepared in a similar experiment was purified by column chromatography to afford pure Compound VIII A acetate; NMR (90 MHz, $CDCl_3$): 2.03 (s, 3), 2.53 (s, 3), 3.83 (s, 3), 3.93 (s, 3), 4.7 (d, J=9 Hz, 1), 5.9 (br., 1), 6.03 (d, J=9 Hz, 1), 6.8-7.1 (br., 3); IR (film) 2940, 1725, 1635, 1575 cm$^{-1}$.

14 (VIII B). A solution of 7.00 g of the product of Example 12 containing VII B in 20 mL of a 1:1 mixture of acetic anhydride and trifluoroacetic acid (v/v) was stirred at room temperature for 1 hour. At the end of this period the volatile material from the reaction mixture was removed by distillation under reduced pressure and the residue was dissolved in dichloromethane. This solution was shaken with a solution of saturated sodium carbonate and the organic layer was separated. The aqueous layer was extracted with dichloromethane (3×100 mL). The combined organic layers were dried and concentrated under reduced pressure to obtain a product which was chromatographed over a silica gel column. Elution with 9:1 hexane:acetone (v/v) mixture containing 5% triethylamine afforded 3.80 g (59% yield) of pure Compound VIII B acetate; NMR (90 MHz, $CDCl_3$): 1.90 (s, 3), 2.53 (s, 3), 3.8 (s, 3), 3.9 (s, 3), 4.83 (d, J=6, 1), 5.63 (t, J=6 Hz, 1), 5.9 (d, J=9, 1), 6.7-7.1 (br., 2). IR: 2980, 1720, 1630, 1575 cm$^{-1}$.

EXAMPLES 15 AND 16

Synthesis of (4aR*,5S*) and (4aR*,5R*)-4a-(2,3-Dimethoxy-phenyl)-2,3,4,4a,5,6,7,8-octahydro-2-methyl-5-iso-quinolinol, acetate, (IX A and IX B; $R^{15}$-OAc) (Step g)

15 (IX A). A solution of 7.40 g (0.017 mol) of the Compound VIII A bromoacetate, from Example 11, and 7.5 g of $K_2CO_3$ in 75 mL of acetonitrile was refluxed for 16 hours. At the end of this period the reaction mixture was cooled to room temperature and diluted with 75 mL of acetone. The reaction mixture was filtered and the residue was washed with acetone (3×50 mL). The combined filtrates were evaporated to obtain 6.50 g of an oil which was crystallized from 50 mL of ethanol to afford 5.53 g (92% yield) of Compound IX A acetate, as crystalline solid, mp 139°-141°. A sample prepared in a similar experiment showed NMR (90 MHz, $CDCl_3$): 2.10 (s, 3), 2.50 (s, 3), 3.83 (s, 3), 3.93 (s, 3), 5.9 (s, 1), 6.6 (d, J=3 Hz, 1), 6.7-7.0 (br., 3). MS (CI) m/z 345. A single crystal obtained from ethanol was subjected to X-ray diffraction analysis and shown to have the assigned structure. The crystals were monoclinic, space group $P2_1/c$, with the following unit-cell parameters at −100°: a=11.166(2), b=9.34(1), c=17.984(2), α=90.0°, β=97.40(1)°, γ=90.0°.

16 (IX B). A solution of 1.00 g (2.34 mmol) of Compound VIII B, from Example 14, in 20 mL of acetonitrile was refluxed for 1 hour in the presence of 1.0 g of $K_2CO_3$. At the end of this period the reaction mixture was cooled to room temperature, and diluted with dichloromethane, and filtered. The filtrate was evaporated to obtain 0.74 g of a solid which was purified by chromatography over silica gel. Elution with a 9:1 mixture of hexane and acetone (v/v) containing 5% triethylamine afforded 0.42 (52% yield) of Compound IX B acetate. A sample prepared in a similar experiment showed NMR (90 MHz, $CDCl_3$): 1.91 (s, 3), 2.60 (s, 3), 3.76 (s, 3), 3.83 (s, 3), 5.36 (d,d, J=6, 3 Hz, 1), 5.8 (s, 1), 6.7-7.31 (br., 3); IR (film): 2980, 1730, 1655, 1575 cm$^{-1}$.

EXAMPLE 17

Synthesis of (4aR*,5S*,8aS*)-4a-(2,3-Dimethoxyphenyl)-decahydro-2-methyl-5-isoquinolinol, acetate (X; $R^{15}$=OAc)

(Step h)

A solution of 1.2 g (3.46 mmol) of Compound IX A acetate in 25 mL of anhydrous ethanol was hydrogenated over $PtO_2$ at a hydrogen pressure of 40 psi (280 kPa) for 16 hours. At the end of this period the catalyst was filtered and the solvent was evaporated to afford 1.18 g (98% yield) of Compound X acetate, mp 111°-116°. A sample prepared in a similar manner showed NMR (90 MHz, $CDCl_3$): 2.13 (s, 3), 2.27 (s, 3), 3.8 (s, 3), 3.9 (s, 3), 5.8-5.9 (br., 1), 6.72-7.1 (br., 3).

EXAMPLE 18

Synthesis of (12bR*)3-methyl-2,3,4,4aα,5,6,7,7aα-octahydro-1H-benzo[4,5]fluoro[3,2-e]isoquinolin-9-ol A solution of 0.80 g (2.3 mmol) Compound X acetate ($R^{15}$=OAc) in 10 mL of dimethylformamide was treated with 0.76 g (10 mmol) of n-propyl mercaptan followed by 0.56 g of potassium t-butoxide. The reaction mixture was heated under nitrogen atmosphere at a temperature of 130° to 140° for 3 hours. At the end of this period the reaction mixture was cooled to room temperature and then treated with 2 mL of acetic acid. The volatile material was distilled off from the reaction mixture under vacuum and the residue was suspended in water. This aqueous suspension was acidified with 50 mL of 10% hydrochloric acid and then extracted with 25 mL of ether. The ether layer was washed with 25 mL of water and the combined aqueous layers were made basic with $Na_2CO_3$. This aqueous layer was extracted with dichloromethane (4×100 mL) and the organic layers were dried ($K_2CO_3$). The combined organic layers were concentrated under reduced pressure to produce 0.61 g of a pink solid. This oil was dissolved in 4 mL of ethanol and upon standing afforded 0.225 g of a solid mp 214°-218°. The mother liquor was concentrated to obtain an additional 0.110 g of a solid, mp 212°-216°. The total yield of the solid was 0.335 g (56% yield). The NMR of a sample prepared in a similar experiment was identical to that of Compound I ($R^2$=OH) prepared as in U.S. Pat. No. 4,243,668.

EXAMPLE 19

Synthesis of
(12bR*)9-Methoxy-3-methyl-2,3,4,4aα,5,6,7,7aα-octahydro-1H-benzo[4,5]furo[3,2e]isoquinoline (I) (Step i)

A solution of 1.4 g (4.03 mmol) of Compound X acetate in a mixture of 25 mL of dichloromethane and 2.5 mL of methanesulfonic acid was stirred at room temperature for 20 hours and then heated at reflux for 6 hours. At the end of this period the reaction mixture was diluted with dichloromethane and made basic with a solution of sodium carbonate. The aqueous layer was extracted with dichloromethane 3×50 mL and the organic layers were dried ($K_2CO_3$). The combined organic layers upon concentration under reduced pressure afforded 1.32 g of product which was subjected to chromatography over silica gel. Fractions containing a total of 0.120 g of the desired product were collected (11% yield). The NMR of this sample was identical to the NMR of Compound I prepared by the procedure of U.S. Pat. No. 4,243,668. MS (CI) m/z 273.

EXAMPLES 20 AND 21

Synthesis of
(7aα,12bR*)2,3,5,6,7,7a-hexahydro-3-methyl-1H-benzo[4,5]furo[3,2-e]isoquinoline-9-ol; (IX; XI; $R^2$=OH)

20 (From IX A). A solution of 0.345 g (1.00 mmol) of compound IX A acetate in 10 mL of dimethylformamide was treated with 0.38 g (5.00 mmol) of n-propyl mercaptan followed by 0.28 g (2.5 mmol) of potassium t-butoxide. The reaction mixture was heated at a temperature of 140° to 150° for 3 hours. At the end of this period the reaction mixture was cooled to room temperature and the volatile material was removed under reduced pressure. The residue was suspended in a saturated solution of $Na_2CO_3$ and extracted with dichloromethane (3×25 mL). The organic layers were dried ($K_2CO_3$) and concentrated under reduced pressure. The product was chromatographed to obtain 0.245 g (95% yield) of Compound XI ($R^2$=OH). A sample prepared in a similar experiment showed NMR (90 MHz, $CDCl_3$): 2.6 (s, 3), 4.5 (d,d J=9,6 Hz), 1), 5.93 (s, 1), 6.66–6.83 (br., 3), 6.9 (s, 1). IR: 2960, 1650, 1600 $cm^{-1}$.

21 (From IX B). A solution of 1.64 g (4.75 mmol) of Compound IX B in 25 mL of dimethylformamide was treated with 1.8 g (23.7 mol) of n-propyl mercaptan and 1.33 g (11.80 mmol) of potassium t-butoxide. The reaction mixture was heated at 120°–130° for 3 hours. At the end of this period the reaction mixture was cooled and the volatile material was distilled off. The residue was suspended in 25 mL of saturated $Na_2CO_3$ and extracted with dichloromethane (3×25 mL). The organic layers were dried ($K_2CO_3$) and concentrated under reduced pressure to afford 1.37 g of an oil. This oil was purified by chromatography over silica gel. Elution with 4:1 hexane/acetone (v/v) mixture containing 5% triethylamine afforded two fractions of 0.27 g and 0.52 g respectively. The NMR, IR and MS of the first fraction showed the presence of Compound XI; thin layer chromatographic analysis of the second fraction showed the presence of the same material. Both were believed to be contaminated with sulfur. The two fractions were combined and used in the next step.

EXAMPLE 22

Synthesis of
(12bR*)-3-Methyl-2,3,4,4aα,5,6,7,7aα-octahydro-1H-benzo[4,5]furo[3,2-e]isoquinolin-9-ol, (I; $R^2$=OH)

A solution of 0.52 g (2.0 mmol) of Compound XI, from Example 21, in 10 mL of ethanol was hydrogenated over 50 mg of $PtO_2$ at a hydrogen pressure of 40 psi (280 kPa) for 48 hours. At the end of this period the reaction mixture contained starting material. Additional amounts (about 50 mg) of $PtO_2$ were added and the hydrogenation was continued for an additional 72 hours. At the end of this period the reaction mixture was filtered and the solvent was removed under reduced pressure to afford 0.51 g of a brown oil which upon dilution with acetone deposited 0.32 g of a solid, mp 212°–216°. The NMR of the solid recrystallized from ethanol was identical to the NMR of the Compound I ($R^2$=OH) prepared by the procedure of U.S. Pat. No. 4,243,668.

EXAMPLE 23

Synthesis of
(12bR*)-3-methyl-2,3,4,4aα,5,6,7,7aα-octahydro-1H-benzo[4,5]furo[3,2-e]isoquinolin-9-ol (I; $R^2$=OH) (Step i)

A solution of 47.0 g (0.136 mol) of Compound X in 470 mL of dimethylformamide was treated with 61.65 mL (51.79 g, 0.681 mol) of n-propyl mercaptan followed by 52.31 g (0.466 mol) of potassium t-butoxide. The reaction mixture was heated under reflux at about 130° to 140° for 4.5 hours and then cooled to room temperature. The volatile material was removed under reduced pressure and the residue was treated with 47 mL of water followed by 47 mL of concentrated hydrochloric acid. The resulting solution was diluted with an additional 100 mL of water and then made basic with $Na_2CO_3$ solution. The precipitate was filtered and dried under reduced pressure to afford 32.00 g (90.7% yield) of a solid mp 210°–213°. The NMR spectrum of this sample was identical to the NMR of the Compound I ($R^2$=OH) prepared by the procedure of U.S. Pat. No. 4,243,668.

BEST MODE

The best mode for carrying out the invention is illustrated by Examples 1 through 5, 8, 10, 13 and 15 followed by, to prepare Compound I, 17 and 23, or, 20 and 22.

UTILITY

The process of the invention is useful in the preparation of analgesic and narcotic antagonistic compounds. The intermediates of the invention are useful in the process.

While the preferred embodiments of the invention are illustrated by the above, it is to be understood that the invention is not limited to the precise construction herein disclosed and that the right to all modifications coming within the scope of the appended claims is reserved.

We claim:
1. The compound, Compound IV, having the formula:

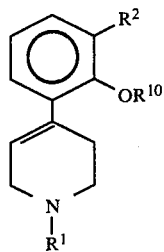
wherein
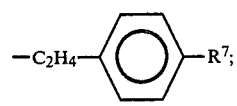
$R^1$ is $C_{1-10}$ alkyl, —$CH_2R^6$ or
$R^2$ is $C_{1-12}$ alkoxy;
$R^6$ is $C_{3-6}$ cycloalkyl, phenyl or 2-tetrahydrofuryl optionally substituted with a methyl group;
$R^7$ is —H or $C_{1-3}$ alkyl; and
$R^{10}$ is $C_{1-10}$ alkyl.
* * * * *